(12) United States Patent
Biedermann et al.

(10) Patent No.: US 9,848,892 B2
(45) Date of Patent: *Dec. 26, 2017

(54) BONE ANCHORING ELEMENT

(75) Inventors: Lutz Biedermann, VS-Villingen (DE); Jürgen Harms, Karlsruhe (DE); Helmar Rapp, Deißlingen (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 638 days.

This patent is subject to a terminal disclaimer.

(21) Appl. No.: 10/494,456

(22) PCT Filed: Dec. 20, 2002

(86) PCT No.: PCT/EP02/14676
§ 371 (c)(1),
(2), (4) Date: Aug. 11, 2004

(87) PCT Pub. No.: WO2004/032774
PCT Pub. Date: Apr. 22, 2004

(65) Prior Publication Data
US 2005/0055026 A1 Mar. 10, 2005

(30) Foreign Application Priority Data
Oct. 2, 2002 (DE) .................. 102 46 177

(51) Int. Cl.
*A61B 17/56* (2006.01)
*A61B 17/16* (2006.01)
(Continued)

(52) U.S. Cl.
CPC ...... *A61B 17/1659* (2013.01); *A61B 17/1671* (2013.01); *A61B 17/1757* (2013.01);
(Continued)

(58) Field of Classification Search
USPC .............. 606/61, 72, 73, 300–321, 264–275; 411/383, 386, 396, 397, 480
See application file for complete search history.

(56) References Cited

U.S. PATENT DOCUMENTS 1,394,608 A * 10/1921 Davern ......................... 411/390
2,292,102 A * 8/1942 Cluett ....................... 174/153 G
(Continued)

FOREIGN PATENT DOCUMENTS

AU 744371 11/1998
DE 43 07 576 C1 4/1994
(Continued)

OTHER PUBLICATIONS

Partial Translation of DE 299 03 855 UI, listed above.
Boothroyd et al., Product Design for Manufacture and Assembly, 1994, Marcel Dekker, Inc., pp. 64 and 77.

*Primary Examiner* — Anu Ramana
(74) *Attorney, Agent, or Firm* — Lewis Roca Rothgerber Christie LLP

(57) ABSTRACT

An anchoring element includes a screw having a shank with a bone thread portion and a head. The anchoring element also includes a receiving part for connecting the screw to a rod-shaped element, the screw and the receiving part being connected to one another in a polyaxial or monoaxial manner, and the shank of the screw being of tubular design and its wall having a plurality of recesses. The bone anchoring element provides for the bone screw to fuse with the surrounding bone substance, and at the same time bone portions or vertebrae can be positioned relative to one another and fixed. Moreover, a substance to be introduced into the bone can be introduced precisely at the desired site.

24 Claims, 6 Drawing Sheets

(51) Int. Cl.
  *A61B 17/17* (2006.01)
  *A61B 17/86* (2006.01)
  *A61F 2/44* (2006.01)
  *A61F 2/46* (2006.01)
  *A61B 17/32* (2006.01)
  *A61B 17/70* (2006.01)
  *A61B 17/00* (2006.01)
  *A61B 17/02* (2006.01)
  *A61B 90/00* (2016.01)

(52) U.S. Cl.
  CPC ........ *A61B 17/864* (2013.01); *A61B 17/8685* (2013.01); *A61B 17/1624* (2013.01); *A61B 17/1628* (2013.01); *A61B 17/1662* (2013.01); *A61B 17/320068* (2013.01); *A61B 17/7041* (2013.01); *A61B 2017/0046* (2013.01); *A61B 2017/00477* (2013.01); *A61B 2017/00544* (2013.01); *A61B 2017/00734* (2013.01); *A61B 2017/0256* (2013.01); *A61B 2017/320004* (2013.01); *A61B 2017/320084* (2013.01); *A61B 2090/033* (2016.02); *A61B 2217/005* (2013.01); *A61B 2217/007* (2013.01); *A61F 2/442* (2013.01); *A61F 2/4611* (2013.01)

(56) References Cited

U.S. PATENT DOCUMENTS

| | | | |
|---|---|---|---|
| 2,293,950 A | 8/1942 | Price | |
| 2,993,950 A * | 7/1961 | Forman | 174/138 D |
| 3,057,285 A * | 10/1962 | Wheeler | 454/339 |
| 4,484,570 A * | 11/1984 | Sutter et al. | 606/72 |
| 4,961,740 A | 10/1990 | Ray et al. | |
| 5,015,247 A | 5/1991 | Michelson | |
| 5,129,904 A * | 7/1992 | Illi | 606/72 |
| 5,133,762 A | 7/1992 | Branemark | |
| 5,209,753 A * | 5/1993 | Biedermann et al. | 606/72 |
| 5,246,458 A | 9/1993 | Graham | |
| 5,330,536 A | 7/1994 | Täger et al. | |
| 5,338,197 A | 8/1994 | Kwan | |
| 5,443,467 A * | 8/1995 | Biedermann et al. | 606/65 |
| 5,458,638 A * | 10/1995 | Kuslich et al. | 623/17.11 |
| 5,507,817 A | 4/1996 | Craig et al. | |
| 5,584,831 A * | 12/1996 | McKay | 606/61 |
| 5,647,873 A * | 7/1997 | Errico et al. | 606/264 |
| 5,658,285 A | 8/1997 | Marnay et al. | |
| 5,667,508 A * | 9/1997 | Errico et al. | 606/73 |
| 5,672,176 A | 9/1997 | Biedermann et al. | |
| 5,681,319 A | 10/1997 | Biedermann et al. | |
| 5,683,391 A | 11/1997 | Boyd | |
| 5,735,850 A * | 4/1998 | Baumgartner et al. | 606/61 |
| 5,743,912 A | 4/1998 | Lahille et al. | |
| 5,776,199 A | 7/1998 | Michelson | |
| 5,797,917 A | 8/1998 | Boyd et al. | |
| 5,800,435 A * | 9/1998 | Errico et al. | 606/61 |
| 5,868,749 A * | 2/1999 | Reed | 606/76 |
| 5,871,548 A | 2/1999 | Sanders et al. | |
| 5,885,299 A | 3/1999 | Winslow et al. | |
| 5,906,616 A | 5/1999 | Pavlov et al. | |
| 5,964,767 A | 10/1999 | Tapia et al. | |
| 5,968,047 A | 10/1999 | Reed | |
| 5,968,098 A | 10/1999 | Winslow | |
| 6,019,760 A | 2/2000 | Metz-Stavenhagen et al. | |
| 6,048,343 A | 4/2000 | Mathis et al. | |
| 6,053,916 A | 4/2000 | Moore | |
| 6,063,090 A * | 5/2000 | Schlapfer | 606/61 |
| 6,102,951 A * | 8/2000 | Sutter et al. | 623/18.11 |
| 6,146,383 A | 11/2000 | Studer et al. | |
| 6,187,005 B1 * | 2/2001 | Brace et al. | 606/264 |
| 6,214,012 B1 | 4/2001 | Karpman et al. | |
| 6,248,105 B1 * | 6/2001 | Schlapfer et al. | 606/266 |
| 6,391,058 B1 | 5/2002 | Kuslich et al. | |
| 6,485,494 B1 * | 11/2002 | Haider | 606/302 |
| 6,592,587 B1 * | 7/2003 | Roger | 606/318 |
| 6,605,089 B1 | 8/2003 | Michelson | |
| 6,758,849 B1 | 7/2004 | Michelson | |
| 6,767,369 B2 | 7/2004 | Boyer, II et al. | |
| 6,835,196 B2 | 12/2004 | Biedermann et al. | |
| 6,921,403 B2 | 7/2005 | Cragg et al. | |
| 6,972,035 B2 | 12/2005 | Michelson | |
| 7,166,109 B2 | 1/2007 | Biedermann et al. | |
| 2001/0021852 A1 * | 9/2001 | Chappius | 606/73 |
| 2002/0026193 A1 * | 2/2002 | Barker et al. | 606/61 |
| 2002/0123752 A1 | 9/2002 | Schultheiss et al. | |
| 2002/0143341 A1 | 10/2002 | Biedermann et al. | |
| 2004/0015172 A1 | 1/2004 | Biedermann et al. | |
| 2004/0147929 A1 | 7/2004 | Biedermann et al. | |

FOREIGN PATENT DOCUMENTS

| | | |
|---|---|---|
| DE | 195 40 180 A1 | 5/1996 |
| DE | 299 03 855 U1 | 7/1999 |
| DE | 199 49 285 A1 | 5/2001 |
| DE | 100 55 891 A1 | 6/2002 |
| DE | 101 15 014 A1 | 10/2002 |
| EP | 0 938 872 A1 | 9/1999 |
| FR | 2 820 630 | 8/2002 |
| JP | 7-51292 | 2/1995 |
| JP | 8-215225 | 8/1996 |
| JP | 2620420 | 6/1997 |
| JP | 10-211213 | 8/1998 |
| JP | 11-253454 | 9/1999 |
| JP | 2000-223915 | 8/2000 |
| JP | 2004-524887 | 8/2004 |
| WO | WO 98/35636 | 8/1998 |
| WO | WO 98/48738 | 11/1998 |
| WO | WO 01/12088 A1 | 2/2001 |
| WO | WO 02/11630 A1 | 2/2002 |
| WO | WO 02/38054 A2 | 5/2002 |
| WO | WO 02/054966 A2 | 7/2002 |

\* cited by examiner

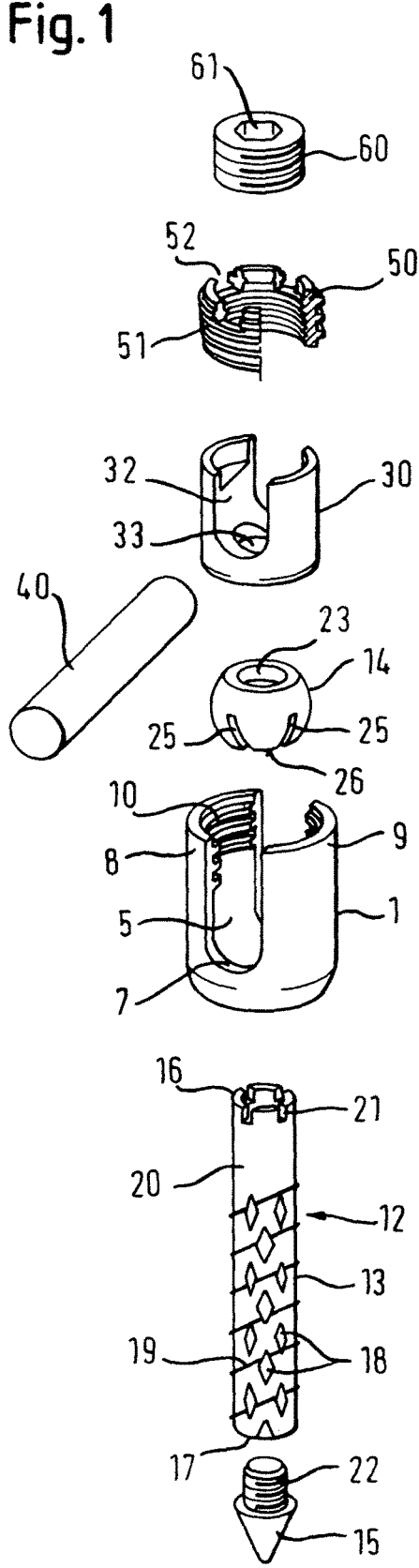
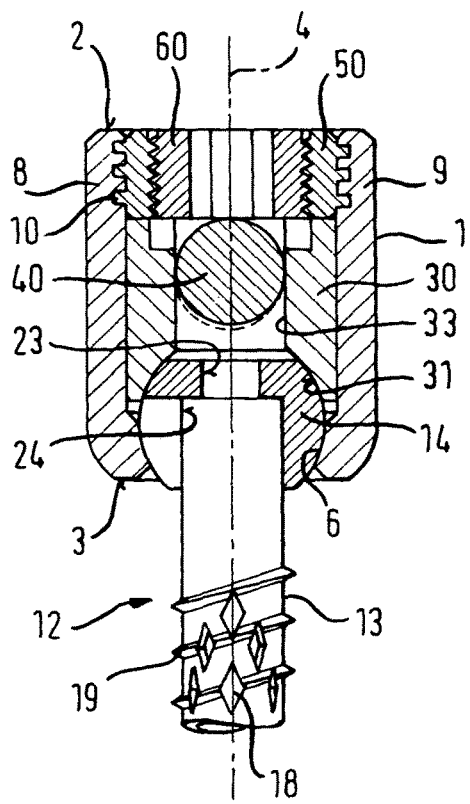

US 9,848,892 B2

BONE ANCHORING ELEMENT

CROSS-REFERENCE TO RELATED APPLICATION(S)

This application is a National Phase Patent Application and claims the priority of International Application Number PCT/EP02/14676, filed on Dec. 20, 2002, which claims priority of German Patent Application Number 102 46 177.5, filed on Oct. 2, 2002.

BACKGROUND OF THE INVENTION

The invention relates to an anchoring element comprising a screw having a shank with a bone thread portion and a head, and comprising a receiving part for connecting the screw to a rod. Such an anchoring element is used in particular in surgery of the spinal column, but also in trauma surgery. The invention also relates to a tubular shank element for connection to a tip and for screwing into a bone.

An anchoring element according to the preamble of claim 1 is known from DE 43 07 576 C1, for example.

A known treatment method for treating bone defects, in particular osteoporotic fractures, involves injecting bone cement and/or medicinal active substances, in particular growth-promoting substances, into the bone. In the area of the spinal column in particular, this requires an exact positioning of the substance to be injected in the vertebra. Moreover, it is in many cases necessary to additionally stabilize the defective vertebrae and fix them relative to one another.

DE 100 55 891 A1 discloses a bone screw with a tubular thread portion which has a bone thread and a plurality of openings provided in the wall of the thread portion.

Based on the above, there is a need for an anchoring element of the type described above in such a way that it can be used in particular in the treatment of osteoporotic fractures.

SUMMARY OF THE INVENTION

This In accordance with the present invention, it is possible for the bone screw to fuse with the surrounding bone substance, and at the same time bone portions or vertebrae can be positioned relative to one another and fixed. Moreover, a substance to be introduced into the bone can be introduced precisely at the desired site. Moreover, a shank element can be used for such an anchoring element.

BRIEF DESCRIPTION OF THE DRAWINGS

Further features and particulars of the invention are set out in the description of illustrative embodiments with reference to the figures. In the figures:

FIG. 1 shows an exploded view of a first embodiment of the anchoring element;

FIG. 2 shows a side view of the anchoring element from FIG. 1, in cross section;

DETAILED DESCRIPTION

Figure 3:
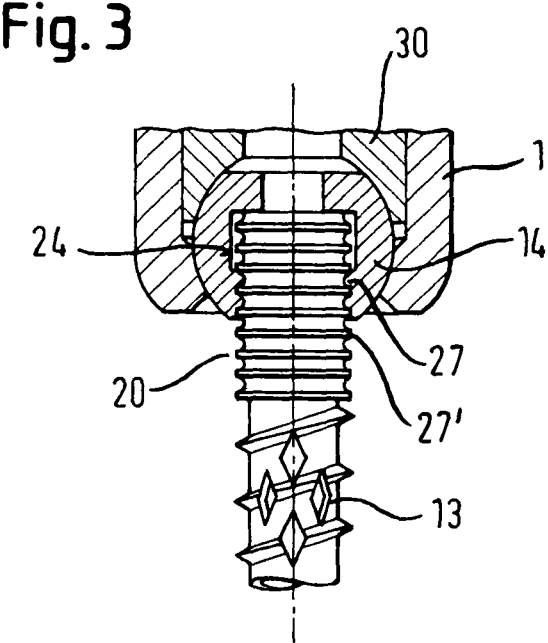
FIG. 3 shows a detail of a modification of the anchoring element according to FIG. 1, in cross section.

In the first embodiment shown in FIGS. 1 and 2, the anchoring element has a cylindrically shaped receiving part 1 with a first end 2 and an opposite, second end 3. The two ends extend perpendicular to an axis of symmetry or longitudinal axis 4. A first coaxial bore 5 is provided which extends, coaxially with respect to the longitudinal axis 4, from the first end 2 to a predetermined distance from the second end 3. Provided at the second end 3 there is a second bore 6 whose diameter is smaller than the diameter of the first bore. In the embodiment shown, the second bore is designed as an opening whose edge is shaped as a hollow sphere segment, the midpoint of which is oriented toward the first end 2.

The receiving part 1 has, starting from the first end 2, a U-shaped recess 7 extending perpendicular to longitudinal axis 3, with two free legs 8, 9 ending toward the first end 2. Adjacent to the first end 2, the branches have an inner thread 10. The inner thread is designed, for example, as a flat thread with thread flanks extending in each case at an angle of 90° to the axis of symmetry 4. The bottom of the U-shaped recess extends to a predetermined distance from the second end 3.

The screw 12 cooperating with the receiving part 1 has a screw shank 13 with a thread portion, and has a head 14 in the shape of a segment of a sphere which, in the assembled state shown in FIG. 2, is connected to the screw shank, and it also has a tip 15.

The screw shank 13 is of tubular design and has a first end 16 directed toward the head 14, and an end 17 remote from the end 16. In its wall the tubular screw shank 13 has a plurality of recesses 18 which, in the embodiment shown, are diamond-shaped. The diamonds are oriented here in such a way that in each case an axis of symmetry extends parallel to the axis of symmetry of the tube. In the axial direction, the recesses 18 are mutually staggered in such a way that an opening is in each case present between the openings of the preceding row of openings arranged in the circumferential direction. On the outer wall, in an area extending front the second end 17 of the screw shank 13 to at least a predetermined distance from the first end 16, there is a so-called bone thread 19 which corresponds in its form to the bone threads of conventional bone screws. In the embodiment shown, the tubular screw shank 13 also has, adjacent to the first end 16, a portion 20 in which no bone thread 19 is formed and whose surface is principally smooth. Moreover, for screwing the screw into the bone, slits 21 for a screwdriver are provided at the first end 16.

The tip 15 comprises the tip part itself and also a shank 22 which, in the illustrative embodiment shown, has a metric outer thread. On its inner wall, adjacent to the second end 17, the tubular screw shank 13 has a portion with a corresponding metric inner thread, and, in the assembled state, the tip is screwed securely to the tubular screw shank.

As can best be seen from FIG. 1, the head 14 is designed as a sphere, flattened at its end to be directed toward the first end 2 of the receiving part 1, and has a first bore 23 extending coaxially with respect to the longitudinal axis 4 and with a diameter smaller than the diameter of the tubular screw shank 13. A coaxial second bore 24 is also provided which, from that end of the head 14 directed toward the second end 3 of the receiving part in the assembled state, extends by a predetermined distance into the head and whose diameter is equal to the external diameter of the tubular screw shank 13 in the portion 20, so that the portion 20 of the screw shank can be pushed with a frictional fit into the bore 24. As can be seen from FIG. 1, the head 14 thus shaped as a hollow sphere segment is provided, on its side remote from the flattened end, with cuttings 25 arranged at a distance from one another in the circumferential direction, extending parallel to the longitudinal axis 4, and reaching as far as the end remote from the flattened side. In this way, the edge 26 directed away from the first end 2 of the receiving part in the assembled state is designed such that it is able to resiliently yield outward in order to permit insertion of the screw shank 13.

A pressure element 30 is also provided which is of cylindrical design and has an external diameter which is exactly such that the pressure element can be inserted into the first bore 5 and can be moved to and fro in the latter in the axial direction. On its underside directed toward the second end 3, the pressure element 30 has a portion 31 shaped as a hollow sphere segment which is symmetrical to the longitudinal axis 4 and whose radius corresponds to the radius of the head 14. The pressure element also has a U-shaped recess 32 which extends transversely with respect to the longitudinal axis 4 and whose free legs extend toward the first end 2 and form a channel in which a rod 40 is to be received. The depth of the U-shaped recess is greater than the diameter of the rod 40 to be inserted, so that, in the assembled state, the legs of the pressure element 30 project above the inserted rod 40. At the bottom of the U-shaped recess 32 there is a coaxial bore 33 used for engagement with a screwing tool.

To fix the position of the head 14, with inserted screw shank 13, relative to the receiving part 1, a nut 50 can be screwed in between the legs 8, 9 of the receiving part, said nut 50 being provided with an outer thread 51 which cooperates with the inner thread 11 of the legs. At one end, the nut has slits 52 for engagement with a screwing tool.

An internal screw 60 for screwing into the nut 50 is also provided, having an outer thread which cooperates with the inner thread of the nut 50. The internal screw 60 has a recess 61 for engagement with a screwing tool.

Upon use, the screw 12 is first screwed into the bone or vertebra. Bone cement or another filler and/or an active substance is then injected into the tubular shank via a syringe. The receiving part 1 is then placed with the second bore 6 onto the shank 13, and the head 14 is guided onto the shank 13, from the direction of the first end 2, so that the shank 13 is inserted via its portion 20 without bone thread into the bore 24 and the head encloses the shank in the manner shown in FIG. 2. The head 14 and the shank 13 are connected to one another with a frictional fit. The pressure element 30 is then fitted and, by means of the nut 50 being screwed in, is pressed onto the head 14 provided with the slits 25 such that said head 14 is securely connected or clamped to the shank 13 and at the same time is pressed against the hollow sphere segment in the receiving part and thus arrested in its rotational position. The rod 40 is still freely displaceable. Said rod 40 is then fixed by the internal screw 60 being screwed in. The anchoring element thus permits treatment of a defective bone with an active substance and/or stabilization by fusion with surrounding bone substance and, at the same time, positioning and fixation of bone pieces or of vertebrae via the rod.

The modification shown in FIG. 3 differs from the embodiment shown in FIGS. 1 and 2 in that the inner wall of the bore 24 of the head 14 is designed with corrugations 27 provided in the circumferential direction, and the portion 20 of the shank 13 is provided with corresponding corrugations 27'.

Figure 4:
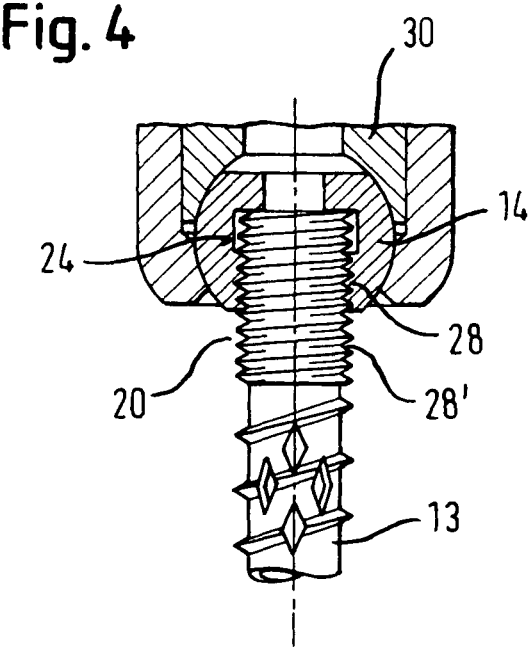
FIG. 4 shows a detail of a further modification of the anchoring element according to the first embodiment, in cross section.

In the modification shown in FIG. 4, the head 14 and the shank 13 have matching threads 28, 28' instead of the corrugations, so that the shank can be screwed into the head.

The screw shank 13 can also have other means by which it is screwed into the bone. For example, the screw shank 13 can also have an inner thread adjacent to its first end or can have an inner thread extending the entire axial length. In this case, the shank can be screwed into place via a head or other auxiliary instrument which is screwed into it and which is removed again after screwing. Alternatively, it is possible for the screw shank 13 to have, adjacent to its first end, an internal hexagon shape for engagement with an Allan key.

Before screwing, it is also possible for the screw shank 13 to be filled with bone substance which, after screwing, then fuses with the bone substance surrounding the screw.

Figure 5:
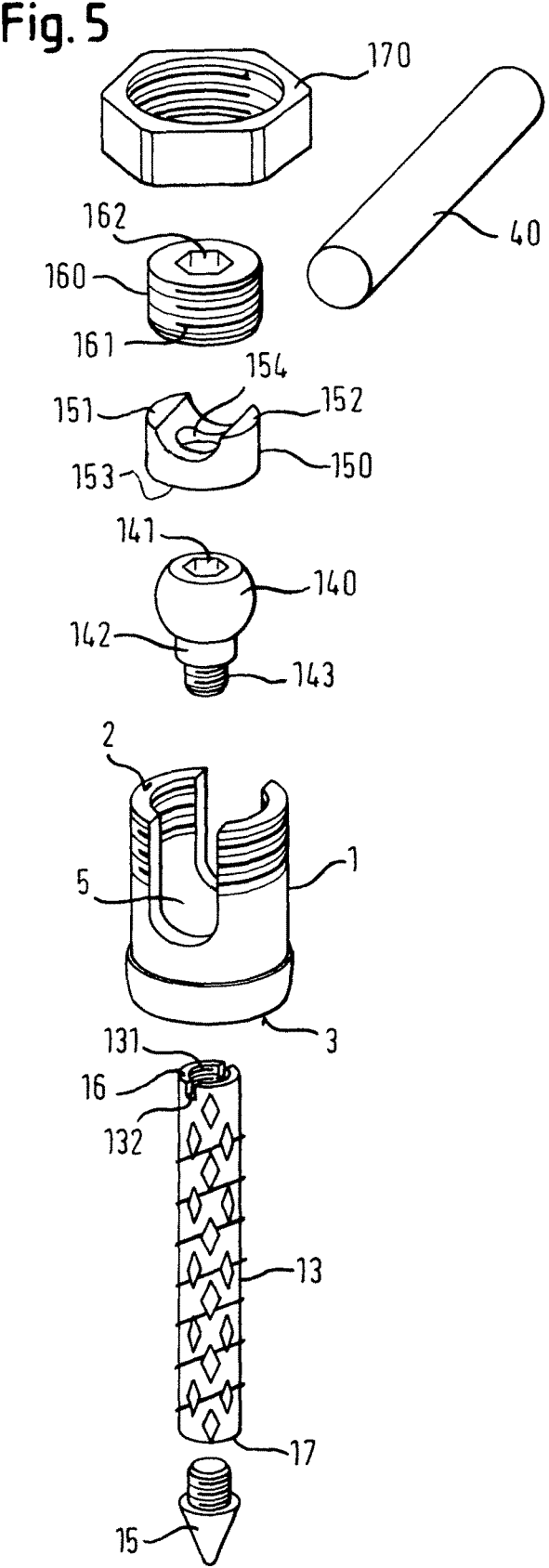
FIG. 5 shows an exploded view of a second embodiment.
Figure 6:
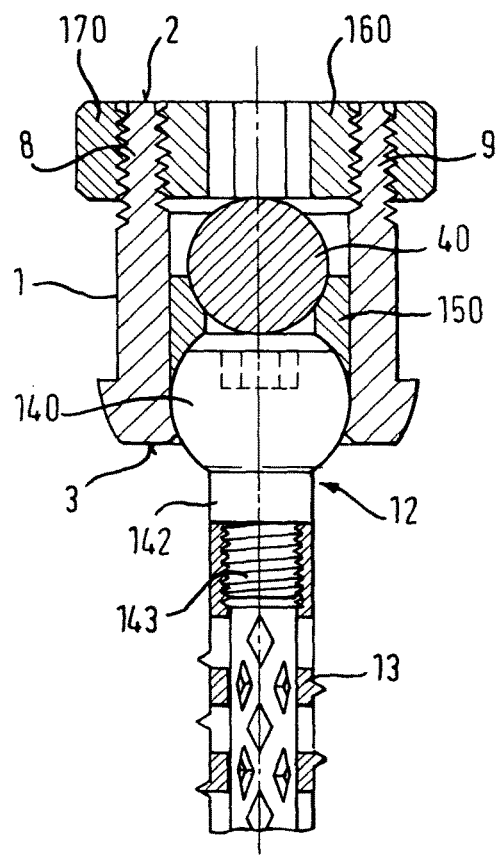
FIG. 6 shows a side view of the second embodiment of the anchoring element, in cross section.

The embodiment shown in FIGS. 5 and 6 differs from the embodiment shown in FIGS. 1 and 2 principally in terms of the design of the screw head 140 and its connection to the screw shank 13.

The screw head 140 is designed in the shape of a segment of a sphere, with a sphere radius which is substantially equal to the radius of the portion of the receiving part shaped as a hollow sphere segment. At its flattened end to be directed toward the first end 2 of the receiving part 1, the head also has a recess 141 for engagement with a screwdriver. At its opposite end, the screw head 140 has a cylindrical neck 142 with an external diameter which corresponds to the external diameter of the tubular screw shank 13. Extending from the neck there is a projection 143 with an outer thread with which the screw head can be screwed into the tubular screw shank 13 which, for this purpose, has on its inner wall, adjacent to its first end 16, an inner thread 131. Thus, in contrast to the first embodiment, the head is connected to the screw shank by means of the head engaging in the shank, whereas in the first embodiment the head engages around the shank.

In this embodiment, the screw head 140 can expediently have a coaxial bore (not shown in the figures) running through it and serving as a channel for the introduction of active substances.

As in the first embodiment, the inner wall adjacent to the second end 17 of the tubular screw shank 13 is likewise provided with an inner thread into which the tip 15 is screwed. Also as in the first embodiment, the inner thread can be formed along the entire length of the tubular thread shank, which is favorable from the point of view of production technology and additionally permits shortening of the tubular screw shank to a desired length. At the first end of the screw shank 13, slits 132 can be provided for engagement with a screwdriver.

The illustrative embodiment depicted shows a variant of the head/rod fixation shown in the first embodiment. In contrast to the pressure element 50 of the first embodiment, the pressure element 150 has only short legs 151, 152, which do not project laterally above the inserted rod 40. Otherwise, the pressure element, as in the first embodiment, has a spherical depression 153, on its side directed toward the head, and a coaxial bore 154.

To fix the head and rod, an internal screw 160 is provided which has an outer thread 161, corresponding to the inner thread of the legs of the receiving part, and a recess for engagement with a screwdriver. To secure the fixation, a locking nut 170 is provided which can be screwed onto the receiving part 1.

Upon use, the tip is first screwed onto the screw shank 13. Then, if necessary, bone substance is introduced into the tubular screw shank, and the head 140 is screwed on. The screw consisting of shank 13, tip 15 and head 140 all screwed together is then introduced like a known polyaxial screw into the receiving part 1 and screwed into the bone. If a cannulated head 140 is used, an active substance or filler can be introduced by injection. Finally, the pressure element is fitted, and the receiving part is connected securely to the rod by screwing the internal screw 160 and the locking nut 170, and the angle position of the head in the receiving part is thus fixed.

Alternatively, if the screw shank has the slits 132 for engagement with a screwdriver, it is also possible for the screw shank 13 with screwed-on tip 15 to be screwed in first without the head 140. The active substance can then be introduced, the receiving part fitted, and the screw head screwed on. The connection to the rod then takes place as described above.

Modifications to the described embodiments are possible. On the one hand, the fixation of the head and rod is not limited to the described variants. The fixation of the head and rod in the second embodiment can also be used in the first embodiment, and vice versa. Moreover, other configurations can also be provided, for example the provision of only and internal screw acting on the rod.

Instead of the diamond-shaped openings in the screw shank, it is also possible to provide circular openings, oval openings, or other openings of any desired shape. The openings can also extend the entire axial length of the screw shank.

The head 14 in the first embodiment can be slotted continuously in the axial direction at one point. The elasticity thus obtained means that the head can be slightly compressed, so that it can be introduced from the direction of the second end 3 of the receiving part.

The tip 15 can be of self-tapping design. Moreover, the tip can have a coaxially extending, continuous channel for active substances to pass through.

The tubular screw shank 13 can have a length suitable for the particular application, said length being obtained if appropriate by cutting a tube portion of desired length from a longer tube portion, and also a diameter corresponding to the application. In particular, the screw can also be designed as a pedicle screw.

To stabilize the spinal column or bones, the anchoring element according to the invention can generally be combined with known anchoring elements via the rod.

Figure 7:
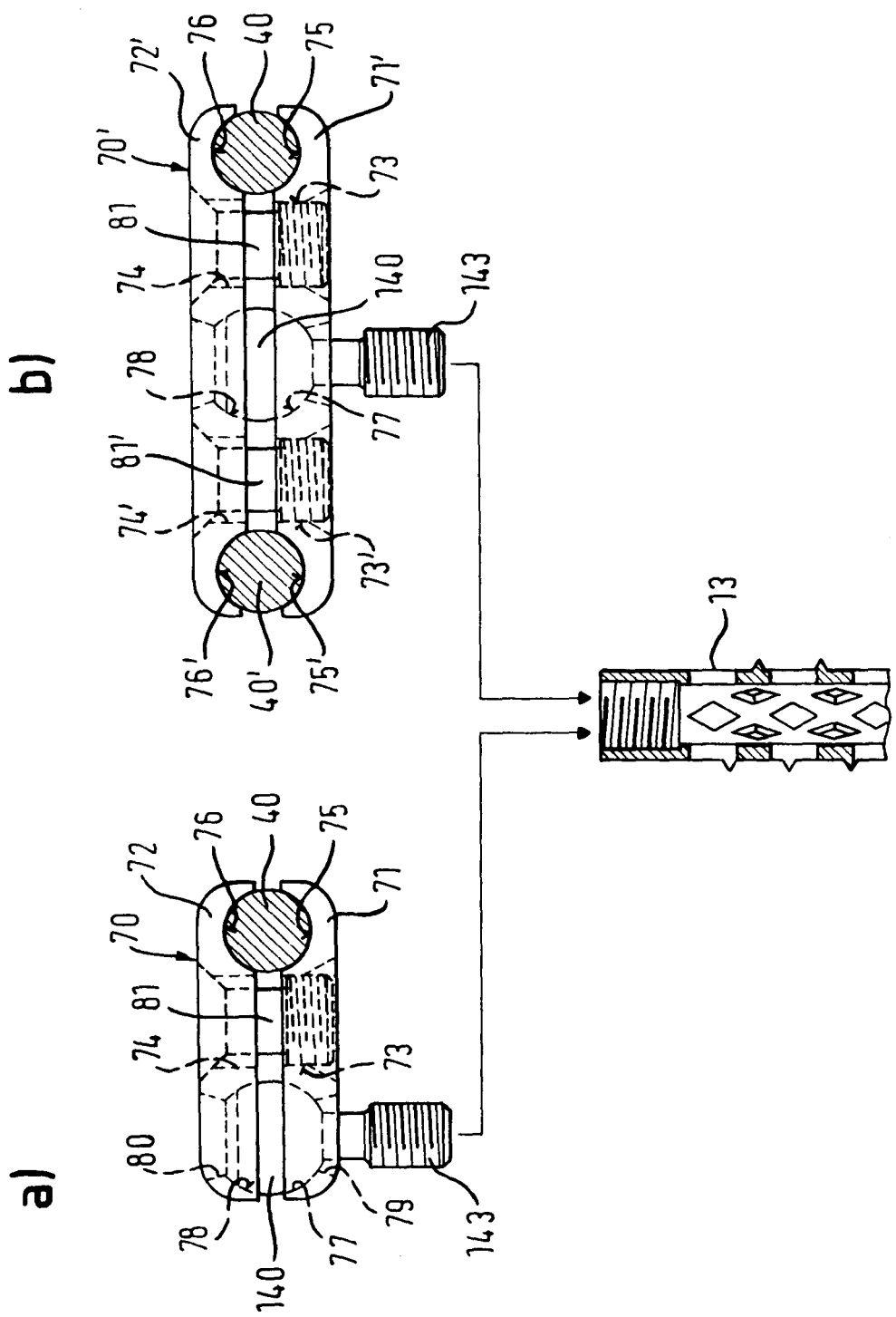
FIG. 7a) shows a third embodiment of the anchoring element.
FIG. 7b) shows a fourth embodiment of the anchoring element.

In the illustrative embodiment shown in FIGS. 7a) and 7b), the polyaxial connection to the rod 40 is not effected in the direction of the screw axis, as in the previous examples, but instead laterally offset with respect to the screw axis.

The anchoring element according to FIG. 7a) comprises a screw element consisting of the tubular screw shank 13, a tip, and the head 140 shaped as a segment of a sphere, and also comprises a two-part holder 70 receiving the head 140, with a lower part 71 directed toward the screw shank and an upper part 72 directed away from the screw shank, which parts together enclose the rod 40. The lower part 71 and the upper part 72 are of identical design and arranged in mirror symmetry with respect to one another. They each have a central bore 73, 74 provided with an inner thread, and, on the surface directed away from the respective other part 71, 72, a countersunk bore. Provided to the side of the bore 73, 74, at a distance therefrom, there is a recess 75, 76 in the shape of a cylinder segment facing toward the respective other part 71, 72 and used for holding the rod 40. To the other side of the bore 73, 74, the lower part 71 and the upper part 72 have, on the side directed toward the respective other part, a recess 77, 78 shaped as a segment of a sphere for holding the screw head 40. On the surface directed away from the other part 71, 72, the recess 77, 78 is adjoined coaxially by an outwardly widening recess 79, 80.

The lower part 71 and upper part 72 of the holder are connected to one another by a screw 81 which can be introduced into the inner thread of the upper part and screwed into the inner thread of the lower part. In its part guided through the upper part 72, the screw 81 has a diameter smaller than the diameter of the inner thread of the upper part, and, in its part guided through the lower part, it has an outer thread cooperating with the inner thread of the lower part. The recesses 75, 76 shaped as cylinder segments and the recesses 77, 78 shaped as sphere segments are dimensioned, and arranged relative to one another, in such a way that, in the state in which the rod 40 and the head 140 are held, the lower part 71 and the upper part 72 are oriented parallel to one another and spaced apart from one another.

Upon use, the screw element is first assembled by screwing the tip and the head 140 onto the shank. The upper part and the lower part of the holder are turned through 90° relative to one another by loosening of the screw 81, so that the screw element can be introduced into the lower part. The screw element is introduced until its head 140 lies in the spherical segment shaped recess 77 of the lower part 71. It is then screwed into the bone. The rod 40 is then inserted, and the upper part 72 is turned through 90° to grip the rod. After setting the angle position of the screw head 140 in the holder and the position of the rod, the arrangement is fixed by tightening the screw 81.

The implant is particularly suitable for fixation of fractures of the pelvis and of long bones.

The embodiment shown in FIG. 7b) differs from the embodiment shown in FIG. 7a) in that the holder 70', in order to grip two rods 40, 40', has an intrinsically symmetrically designed lower part 71' and upper part 72'. The lower part 71' and the upper part 72' are in this case designed symmetrical to a plane defined by the midline of the rods 40, 40' and the midpoint of the spherical segment shaped head 140 of the screw, and they each have two bores 73, 73' and 74, 74', respectively, and two cylinder segment shaped recesses 75, 75' and 76, 76', respectively. To fix them, two fixing screws 81, 81' are provided. The operation is analogous to the above-described illustrative embodiment, the only difference being that two rods are to be fixed.

Figure 8:
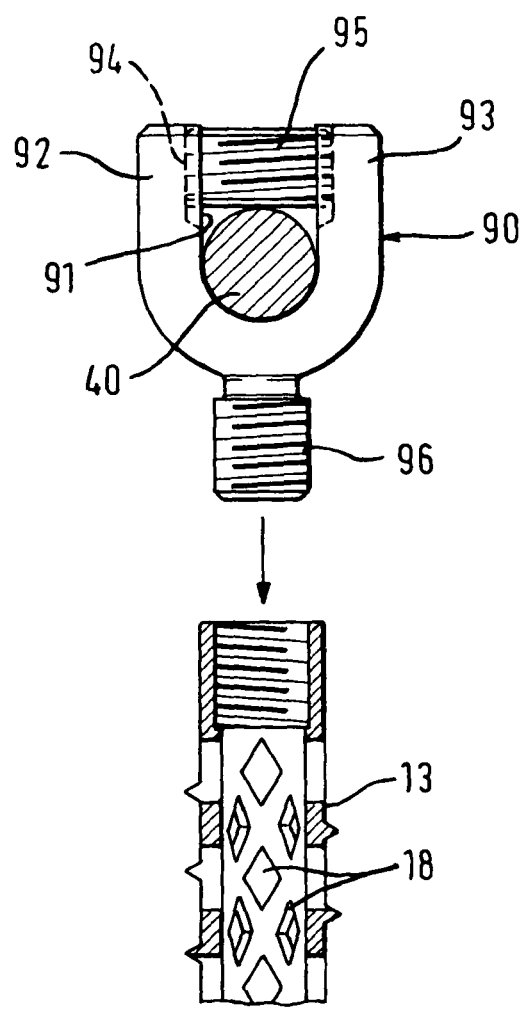
FIG. 8 shows a fifth embodiment of the anchoring element.

In the embodiment shown in FIG. 8, the anchoring element consists of a screw element, formed by the tubular screw shank 13 and a tip connected to the latter, and of a receiving part 90 which can be connected monoaxially to the screw element and receives a rod 40. The receiving part 90 is substantially cylindrical and has a recess 91 with U-shaped cross section which is exactly dimensioned so that the rod 40 can be inserted and fits into the bottom of the recess. Two free legs 92, 93 are formed by the U-shaped recess 91. Adjacent to the free end, the branches 92, 93 have an inner thread 94 which cooperates with a corresponding outer thread of an internal screw 95 to be screwed in between the legs for the purpose of fixing the rod 40. At its end directed way from the free end, the receiving part 90 has a threaded shaft 96 for screwing into the tubular shank 13.

Upon use, the whole anchoring element is preferably assembled first, the tubular shank, if necessary, being filled with active substances or bone substance. The anchoring element is then screwed like a known monoaxial screw into the bone. The connection to one or more other anchoring elements is then made via the rod. In the correct position, the rod is then fixed via the internal screw.

In the embodiments shown in FIGS. 1 to 8, some of the recesses 18 are arranged so that they interrupt the helix crest of the bone thread. Teeth or sharp edges are thus formed on the bone thread, which have a milling effect as the element is being screwed into the bone. For certain applications, however, smooth screwing-in is desired or necessary.

Figure 9:
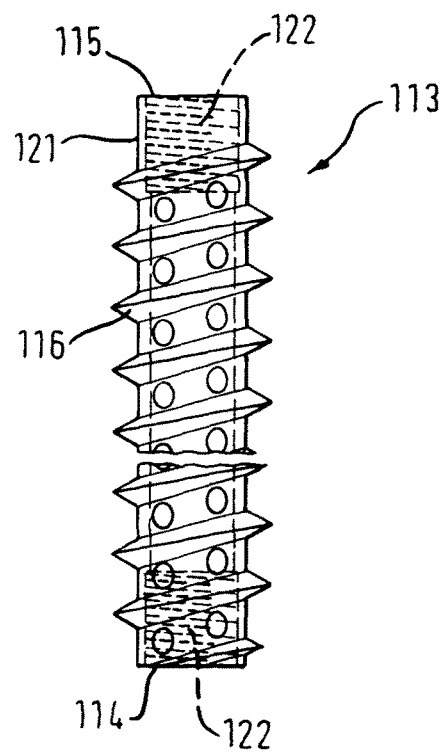
FIG. 9 shows a modification of the above-described embodiments.
Figure 10:
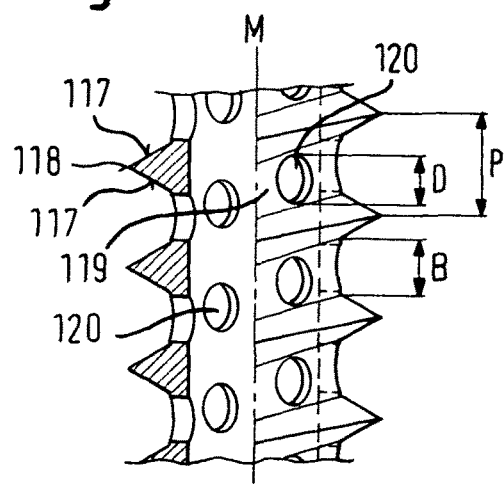
FIG. 10 shows an enlarged, partially cross-sectional view of the modification from FIG. 9.
Figure 11:
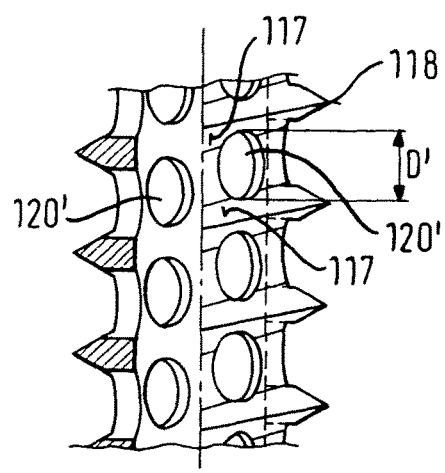
FIG. 11 shows a further modification in an enlarged, partially cross-sectional view.

For applications of this kind, a modification of the tubular screw shank, as shown in FIGS. 9 through 11, is advantageous. The tubular screw shank 113 consists of a cylindrical tube with a first end 114 and, remote from this, a second end 115. As has already been seen in the embodiments in FIGS. 1 through 8, the outer wall of the tube has a bone thread portion 116 with a bone thread for screwing into the bone. The bone thread is designed as a self-tapping thread and has, in a known manner, thread flanks 117, a helix crest 118, a thread root 119 with a width B, and a thread pitch P. In at least the bone thread portion 116, the wall of the tubular shank has a plurality of recesses 120 of circular cross section. The recesses 120 are arranged such that their center in each case lies in the thread root 119, and the diameter D of each recess 120 is smaller than the thread pitch P and in particular not greater than the width B of the thread root, so that, in the illustrative embodiment shown in FIGS. 9 and 10, the recesses 120 lie completely in the thread root 119 and do not extend into the flanks 117. In the thread root 119 of each thread turn, a plurality of recesses 120 are provided which are spaced apart uniformly on the helix line so that, viewed in the axial direction, the recesses of one thread turn are located above the recesses of the thread turn lying below.

As can be seen in particular from FIG. 9, the tubular shank 113 has, adjacent to the first end 115, a portion 121 having no bone thread and having a smooth outer wall in which no recesses are formed. Also, in the illustrative embodiment shown, an inner thread portion 122 is formed adjacent to the first end 114 and adjacent to the second end 115, said inner thread portion 122 serving for connection to the tip and, respectively, to the screw head and receiving part, as has been described with reference to the preceding embodiments.

The other modified embodiment shown in FIG. 11 differs from the embodiment shown in FIGS. 9 and 10 in that the diameter D' of the recess 120' is greater than the width B of the thread root 119, so that the recesses 120' extend into the flanks 117 of the bone thread, but without interrupting the helix crest 118. In this way it is possible for the recesses to be made larger in order to achieve a better fusion with the bone, but formation of teeth with a milling action during screwing is avoided, because the cutting crest of the thread is left intact.

In another modification (not shown), all or some of the recesses 120, 120' are provided on the outside of the wall with a countersink forming a surface roughness which makes fusion easier. The diameter of this countersink in the direction of the screw axis is smaller, however, than the thread pitch P, so that the helix crest 118 is left intact.

In another modification, the recesses are oval or diamond-shaped. The important thing is that they are arranged in the thread root and their dimensions are such that the cutting crest of the bone thread is not damaged. Moreover, recesses do not have to be provided in each thread turn.

In another modification, the bone thread portion 116 extends the entire length of the shank 113. The inner thread 122 can likewise extend the entire length. Alternatively, the inner thread 122 can also be provided only at one end in one portion or can be omitted altogether. In the case where no inner thread is provided, the connection to the other parts of the anchoring element is achieved, for example, by means of a snug fit.

Figure 12:
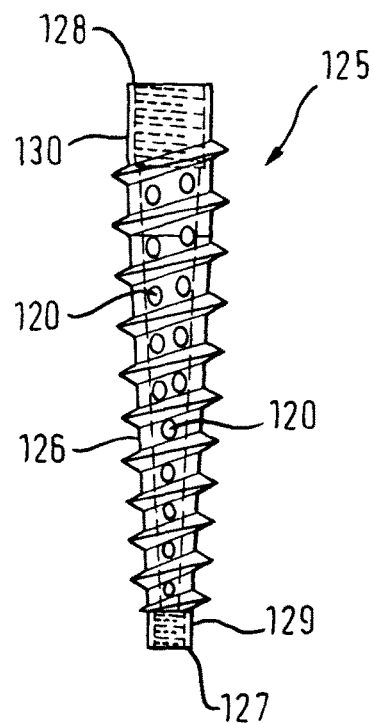
FIG. 12 shows a further modification of the above-described embodiments.

In another modified embodiment of the shank as shown in FIG. 12, the tubular screw shank 125 is not of an entirely cylindrical design, but instead has a conical bone thread portion 126 tapering in the direction toward the end 127 to be connected to the tip. Adjacent to the conical bone thread portion 126, and extending as far as the opposite ends 127, 128, there is in each case a cylindrical portion 129, 130 with an inner thread for connection to the tip at one end and for connection to a head or a receiving part at the other end, as has been described above.

In a modification of this, the cylindrical portion 129 to be connected to the tip is not provided, and instead the free end of the conical bone thread portion 126 itself acts as a tip.

In the embodiment shown in FIG. 12, the recesses 120 are provided on the thread root, as in the embodiments shown in FIGS. 9 through 11. In another modification, the tubular shank 13 shown in FIGS. 1 through 8 is likewise made conical at least in one portion.

The invention claimed is:

1. A bone anchoring element for use in surgery of the spinal column or in trauma surgery comprising:
    a tubular shank element having a proximal end, a distal end, and a shank wall defining an inner cavity extending entirely through the shank element along a longitudinal axis from the proximal end to the distal end,
    the shank wall having a bone thread portion comprising an exterior bone thread having a helix crest and a thread root, the shank wall defining openings completely through the shank wall of the bone thread portion and communicating with the inner cavity;
    a head connectable to the proximal end;
    a tip connectable to the distal end;
    a receiving part configured to be polyaxially coupled to the head and having a U-shaped recess configured to receive a rod, the receiving part further defining an axial bore extending from a first end of the receiving part toward a second end of the receiving part; and
    a pressure element having an underside, the pressure element movable in the axial bore from the first end toward the second end to contact the head in the axial bore with its underside and arrest the head in one of a plurality of polyaxial positions in the axial bore;
    wherein the proximal end of the shank element is configured to engage a tool for driving the shank element into a bone;
    wherein the pressure element has a coaxial bore.

2. The bone anchoring element as claimed in claim 1, wherein at least some of the openings extend into the bone thread in such a way that the helix crest is interrupted.

3. The bone anchoring element as claimed in claim 1, wherein the openings are arranged in the thread root of the bone thread and are structured and arranged so that the helix crest of the bone thread is intact.

4. The bone anchoring element as claimed in claim 1, wherein the bone thread portion of the tubular shank element comprises a conical portion.

5. The bone anchoring element as claimed in claim 1, wherein the proximal end includes an inner thread portion and the head comprises a corresponding outer thread so that the head can be screwed into the shank element.

6. The bone anchoring element as claimed in claim 1, wherein the head comprises a receiving end wall that defines an axial bore configured to receive the proximal end of the shank element.

7. The bone anchoring element as claimed in claim 6, wherein the head comprises a transversely extending end wall configured to engage the proximal end of the tubular shank element to stop the tubular shank element from further axial movement into the axial bore of the head.

8. The bone anchoring element as claimed in claim 6, wherein a portion of the shank element comprises a corrugated outer surface configured to engage an inner surface of the end wall of the head.

9. The bone anchoring element as claimed in claim 6, wherein the receiving end wall has an end that faces the distal end of the shank element when the head and shank element are assembled, wherein the head comprises slits extending axially into and through the end of the receiving end wall of the head, the slits providing a resiliently yielding edge surrounding the axial bore of the head.

10. The bone anchoring element as claimed in claim 6, wherein the axial bore of the head comprises a channel extending axially through the head.

11. The bone anchoring element as claimed in claim 1, wherein the head comprises a U-shaped recess configured to receive a rod.

12. The bone anchoring element as claimed in claim 1 wherein the head is spherical.

13. The bone anchoring element as claimed in claim 1, further comprising a closure element connectable inside the U-shaped recess to secure the receiving part to the head.

14. The bone anchoring element as claimed in claim 1, wherein a diameter of the distal end is less than a diameter of the proximal end.

15. The bone anchoring element as claimed in claim 1, wherein the shank element is tapered between the proximal end and the distal end.

16. The bone anchoring element as claimed in claim 1, wherein a portion of the shank element extending from the proximal end is without bone thread.

17. The bone anchoring element as claimed in claim 1, wherein the tubular shank element is conical and wherein the proximal end and the distal end are cylindrical.

18. The bone anchoring element as claimed in claim 1, wherein the axial bore extends from the first end of the receiving part between two free legs forming the U-shaped recess toward the second end of the receiving part and, in an assembled position, the axial bore simultaneously receives the head adjacent the second end of the receiving part and the rod between the two free legs.

19. The bone anchoring element as claimed in claim 18, further comprising a closure element, wherein, in the assembled position, the closure element is configured to engage the receiving part inside the U-shaped recess between the two free legs to secure the receiving part to the head.

20. The bone anchoring element as claimed in claim 19, wherein the closure element and the receiving part are each threaded for threadable engagement in the assembled position.

21. A bone anchoring element for use in surgery of the spinal column or in trauma surgery comprising:
a tubular shank element having a proximal end, a distal end, and a shank wall defining an inner cavity extending entirely through the shank element along a longitudinal axis from the proximal end to the distal end,
the shank wall having a bone thread portion comprising an exterior bone thread having a helix crest and a thread root, the shank wall defining openings completely through the shank wall of the bone thread portion and communicating with the inner cavity;
a head connectable to the proximal end;
a tip connectable to the distal end;
a receiving part to be pivotally coupled to the head and having a U-shaped recess configured to receive a rod, the receiving part further defining an axial bore extending from a first end of the receiving part toward a second end of the receiving part; and
a pressure element having an underside, the pressure element movable in the bore from the first end toward the second end to contact the head in the bore with its underside and arrest the head in its rotational position in the bore;
wherein the proximal end of the shank element is configured to engage a tool for driving the shank element into a bone and wherein the proximal end of the shank element is sized to enter the bore through the second end of the receiving part for connecting to the head when the head is located in the receiving part;
wherein, in a first assembled position, the head and receiving part are configured such that the head engages the receiving part in the bore for movement between the head and the receiving part in a polyaxial manner and in a second assembled position, the pressure element arrests the head in one of a plurality of polyaxial positions in the bore.

22. The bone anchoring element as claimed in claim 21, further comprising a closure element, wherein the closure element is configured to engage the receiving part in the bore and secure a rod and the head in the bore.

23. The bone anchoring element as claimed in claim 22, wherein the closure element and the receiving part are each threaded for threadable engagement in the assembled position.

24. A bone anchoring element for use in surgery of the spinal column or in trauma surgery comprising:
a tubular shank element having a proximal end, a distal end, and a shank wall defining an inner cavity extending entirely through the shank element along a longitudinal axis from the proximal end to the distal end;
the shank wall having a bone thread portion comprising an exterior bone thread having a helix crest and a thread root, the shank wall defining openings completely through the shank wall of the bone thread portion and communicating with the inner cavity;
a head connectable to the proximal end; and
a tip connectable to the distal end;
a receiving part configured to be coupled to the head, the receiving part having a U-shaped recess at a first end configured to receive a rod and having a bore at a second end opposite the first end;
wherein, in an assembled position, the head and the receiving part are configured such that the head engages the receiving part in the bore for movement between the head and the receiving part in a polyaxial manner;

wherein the proximal end of the shank element is configured to engage a tool for driving the shank element into a bone and wherein the proximal end of the shank element is sized to enter the bore through the second end of the receiving part for connecting to the head when the head is located in the receiving part.

* * * * *